US011202875B2

(12) United States Patent
Kissel et al.

(10) Patent No.: US 11,202,875 B2
(45) Date of Patent: Dec. 21, 2021

(54) COUGH ASSISTANCE AND MEASUREMENT SYSTEM AND METHOD

(71) Applicant: KONINKLIJKE PHILIPS N.V., Eindhoven (NL)

(72) Inventors: Michael Howard Kissel, Swissvale, PA (US); April Stewart Nathan, Pittsburgh, PA (US); Winslow Kevin Duff, Export, PA (US); Bernard F. Hete, Kittanning, PA (US)

(73) Assignee: Koninklijke Philips N.V., Eindhoven (NL)

( * ) Notice: Subject to any disclaimer, the term of this patent is extended or adjusted under 35 U.S.C. 154(b) by 1454 days.

(21) Appl. No.: 14/402,201

(22) PCT Filed: May 14, 2013

(86) PCT No.: PCT/IB2013/053919

§ 371 (c)(1),
(2) Date: Nov. 19, 2014

(87) PCT Pub. No.: WO2013/175345

PCT Pub. Date: Nov. 28, 2013

(65) Prior Publication Data

US 2015/0136134 A1 May 21, 2015

Related U.S. Application Data

(60) Provisional application No. 61/650,079, filed on May 22, 2012.

(51) Int. Cl.
*A61M 16/00* (2006.01)
*A61B 5/087* (2006.01)
(Continued)

(52) U.S. Cl.
CPC ....... *A61M 16/0069* (2014.02); *A61B 5/0823* (2013.01); *A61B 5/0871* (2013.01);
(Continued)

(58) Field of Classification Search
CPC .......... A61M 16/0069; A61M 16/0003; A61M 16/0009; A61M 16/0883; A61M 16/0051;
(Continued)

(56) References Cited

U.S. PATENT DOCUMENTS 5,884,622 A * 3/1999 Younes ................ A61M 16/00 128/204.21
7,011,091 B2 * 3/2006 Hill .................... A61M 16/026 128/204.18
(Continued)

FOREIGN PATENT DOCUMENTS

JP 2010528723 A 8/2010
WO WO2008148134 A1 12/2008
(Continued)

*Primary Examiner* — Elliot S Ruddie
(74) *Attorney, Agent, or Firm* — Daniel H. Brean

(57) ABSTRACT

Systems and methods are configured to inexsufflate a subject and provide cough-by-cough feedback during treatment and/or therapy of the subject. Through sensors that are included in the systems, various gas and/or respiratory parameters maybe measured and/or determined in real-time, such as, for example, peak cough flow and/or inspiratory tidal volume.

15 Claims, 2 Drawing Sheets

(51) Int. Cl.
*A61B 5/08* (2006.01)
*A61M 16/08* (2006.01)
*A61M 16/06* (2006.01)

(52) U.S. Cl.
CPC .... *A61M 16/0003* (2014.02); *A61M 16/0009* (2014.02); *A61M 16/0051* (2013.01); *A61M 16/06* (2013.01); *A61M 16/0883* (2014.02); *A61M 2016/0027* (2013.01); *A61M 2016/0033* (2013.01); *A61M 2016/0036* (2013.01); *A61M 2205/3303* (2013.01); *A61M 2205/3327* (2013.01); *A61M 2205/50* (2013.01); *A61M 2205/502* (2013.01); *A61M 2205/52* (2013.01); *A61M 2230/43* (2013.01)

(58) Field of Classification Search
CPC .......... A61M 16/06; A61M 2016/0027; A61M 2016/0033; A61M 2016/0036; A61M 2205/3303; A61M 2205/3327; A61M 2205/50; A61M 2205/502; A61M 2205/52; A61M 2230/43; A61B 5/0823; A61B 5/0871
See application file for complete search history.

(56) References Cited

U.S. PATENT DOCUMENTS

2007/0017522 A1 1/2007 Be-Eri et al.
2007/0157931 A1* 7/2007 Parker .................. A61M 11/005 128/204.23
2007/0199566 A1* 8/2007 Be'eri .............. A61M 16/0051 128/204.23
2010/0050085 A1* 2/2010 Blike ..................... A61B 5/087 715/738
2011/0138311 A1* 6/2011 Palmer ................... G16H 10/60 715/771
2011/0220107 A1 9/2011 Kimm
2012/0111329 A1 5/2012 Brand
2014/0216451 A1* 8/2014 Jaffe ................ A61M 16/0051 128/202.22
2015/0059753 A1* 3/2015 Hill ..................... A61M 16/024 128/204.23

FOREIGN PATENT DOCUMENTS

WO WO2011045735 A1 4/2011
WO 2011147438 A1 12/2011
WO 2012020387 A1 2/2012

* cited by examiner

COUGH ASSISTANCE AND MEASUREMENT SYSTEM AND METHOD

CROSS-REFERENCE TO RELATED APPLICATIONS

This patent application claims the priority benefit under 35 U.S.C. § 371 of international patent application no. PCT/IB2013/053919, filed May. 14, 2013, which claims the priority benefit under 35 U.S.C. § 119(e) of U.S. Provisional Application No. 61/650,079 filed on May 22, 2012, the contents of which are herein incorporated by reference.

BACKGROUND OF THE INVENTION

1. Field of the Invention

The present disclosure pertains to systems and methods for inexsufflating a subject. In particular, the systems and methods described herein measure, display, and/or record the efficacy of individual inexsufflations quantitatively through various gas and/or respiratory parameters, including, for example, peak cough flow and inspiratory tidal volume.

2. Description of the Related Art

Various systems for increasing patient cough flow through (in)exsufflation are known. Conventional (in)exsufflation is generally accomplished using a single (in)exsufflation event including a single exhalation of the subject. A respiratory circuit and/or the subject may positively pressurize the airway of the subject, and then the respiratory circuit and/or the subject may suddenly reverse the pressure and expel all (or substantially all) of this gas. Secretions built up in the airway of the subject over time may thus be expelled with the gas. Control of the operation of conventional systems used for (in)exsufflation may include setting an inspiratory pressure and/or one or more time parameters related to the duration of inhalation and/or exhalation.

Some characteristics of manual inexsufflation by a subject, without the aid of mechanical and/or electronic assistance, may be quantified using a spirometer. For example, a subject may cough into a spirometer such that, e.g., a peak expiratory flow and/or an expiratory tidal volume may be measured. It is noted that the use of a spirometer is limited by various practical limitations, including but not limited to the limitation that some mechanically ventilated patients may not be able to use a spirometer.

SUMMARY OF THE INVENTION

Accordingly, one or more aspects of the present disclosure relate to a system configured to inexsufflate a subject. The system comprises a pressure generator configured to generate a pressurized flow of breathable gas for delivery to an airway of the subject, a subject interface configured to guide the pressurized flow of breathable gas to the airway of the subject; one or more sensors configured to generate one or more output signals conveying information related to one or more parameters, wherein the one or more parameters include one or both of a gas parameter and/or a respiratory parameter; and one or more processors configured to execute computer program modules. The computer program modules comprise a control module configured to control the pressure generator to inexsufflate the subject, and a parameter determination module configured to determine a peak cough flow parameter based on the one or more output signals.

Yet another aspect of the present disclosure relates to a method of inexsufflating a subject. The method comprises generating a pressurized flow of breathable gas for delivery to an airway of the subject; guiding the pressurized flow of breathable gas to the airway of the subject; generating one or more output signals by one or more sensors conveying information related to one or more parameters, wherein the one or more parameters include one or both of a gas parameter and/or a respiratory parameter; controlling the pressurized flow of breathable gas to inexsufflate the subject; and determining a peak cough flow parameter based on the one or more output signals.

Still another aspect of present disclosure relates to a system configured for inexsufflating a subject. The system comprises pressure means for generating a pressurized flow of breathable gas for delivery to an airway of the subject; means for guiding the pressurized flow of breathable gas to the airway of the subject; sensor means for generating one or more output signals conveying information related to one or more parameters, wherein the one or more parameters include one or both of a gas parameter and/or a respiratory parameter; means for controlling the pressure means to inexsufflate the subject; and means for determining a peak cough flow parameter based on the one or more output signals.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
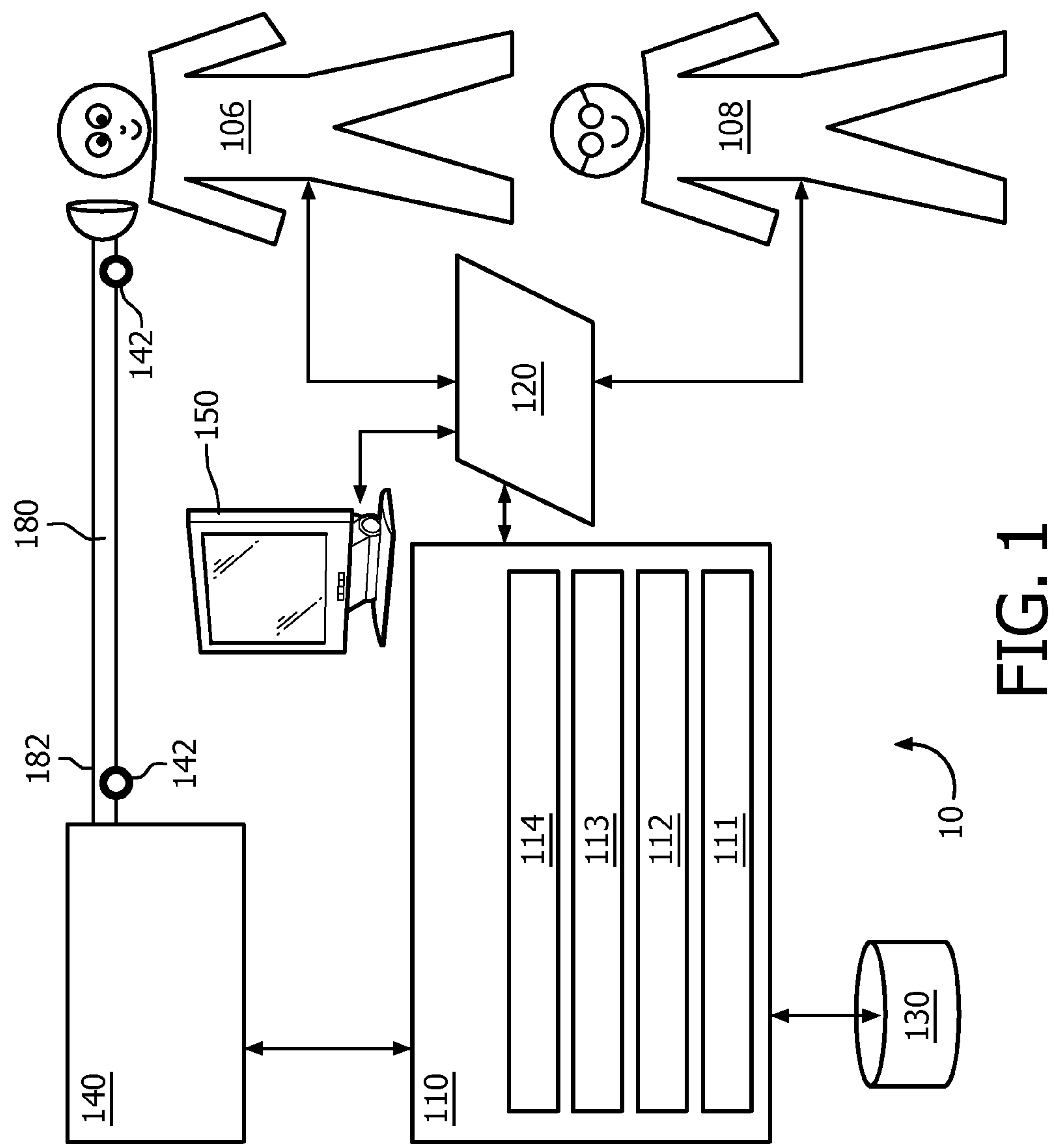
FIG. 1 illustrates a system configured to inexsufflate a subject according to one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary embodiment of a system 10 to inexsufflate a subject 106. Inexsufflation may loosen and/or expel secretions. Unaided inexsufflation may be difficult and/or impossible for a wide range of patients due to a wide range of different medical reasons. The efficacy of an individual inexsufflation (e.g. during an individual respiratory cycle) can be quantified using one or more characteristic parameters, described below. System 10 measures, displays, and/or records information pertaining to individual inexsufflations, sets of such inexsufflations, individual treatments including one or more of such inexsufflations, sets of such treatments, days including one or more such treatments, and/or other periods of treatment time including one or more such individual inexsufflations.

System 10 includes one or more of a pressure generator 140, a user interface 120, a delivery circuit 180, electronic storage 130, one or more sensors 142, one or more processors 110, a control module 111, a parameter determination module 112, an interface module 113, a metric storage module 114, and/or other components. System 10 may be dedicated to providing inexsufflations.

In some embodiments, pressure generator 140 of system 10 in FIG. 1 may be integrated, combined, or connected with a ventilator device or system.

Pressure generator 140 is configured to provide a pressurized flow of breathable gas for fluid communication with the airway of subject 106, e.g. via delivery circuit 180. The direction of the fluid communication may be selectively controlled. Pressure generator 140 may be configured to adjust one or more of pressure levels, flow, humidity, velocity, acceleration, and/or other parameters of the pressurized flow of breathable gas.

Delivery circuit 180 is configured to selectively control the direction and/or flow of breathable gas to and/or from the airway of subject 106. Delivery circuit 180 may sometimes be referred to as subject interface 180. Delivery circuit 180 may be configured to operate in one or more of a first mode, a second mode, a third mode, and/or in other modes. One or more modes may correspond to one or more respiratory phases of a breathing cycle. In the first mode, delivery circuit 180 is closed such that substantially no gas is communicated with the airway of subject 106 therethrough. In the second mode delivery circuit 180 is opened to permit gas to be exhausted from the airway of subject 106 through delivery circuit 180, e.g. to ambient atmosphere. In the third mode delivery circuit 180 is opened to permit gas to be delivered to the airway of subject 106 through delivery circuit 180.

In some implementations, delivery circuit 180 may include one or more of a valve and/or another pressure regulating device. In one embodiment delivery circuit 180 may include multiple valves in series and/or in parallel. Examples of suitable valves and/or other pressure regulating devices include a plug valve, a ball valve, a check valve, a butterfly valve, a solenoid, and/or other pressure regulating devices. Pressure regulating devices may be controlled hydraulically, pneumatically, via an electric motor and/or another mode of control configured to open and/or close a valve and/or other pressure control device.

Delivery circuit 180 may include a conduit 182 and/or a subject interface appliance 184. Conduit 182 may include a flexible length of hose, or other conduit, either in single-limb or dual-limb configuration that places subject interface appliance 184 in fluid communication with pressure generator 140. Conduit 182 forms a flow path through which the pressurized flow of breathable gas (e.g. air) is communicated between subject interface appliance 184 and pressure generator 140.

Subject interface appliance 184 of system 10 in FIG. 1 is configured to deliver the pressurized flow of breathable gas to the airway of subject 106. As such, subject interface appliance 184 may include any appliance suitable for this function. In some embodiments, subject interface appliance 184 is configured to engage the airway of subject 106 without an intervening appliance. In this embodiment, subject interface appliance 184 may include one or more of an endrotracheal tube, a nasal cannula, a tracheotomy tube, a nasal mask, a nasal/oral mask, a full-face mask, a total facemask, and/or other interface appliances that communicate a flow of gas with an airway of a subject. In some embodiments, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endrotracheal tube, a tracheotomy portal, and/or other interface appliances. The present disclosure is not limited to these examples, and contemplates delivery of the pressurized flow of breathable gas to subject 106 using any subject interface.

Electronic storage 130 of system 10 in FIG. 1 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.), a slot (e.g., an SD card slot, etc.), or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store information pertaining to individual inexsufflations and/or treatments that include one or more inexsufflations (as discussed elsewhere herein), and/or other information. Electronic storage 130 may be a separate component within system 10, or electronic storage 130 may be provided integrally with one or more other components of system 10 (e.g., processor 110).

User interface 120 of system 10 in FIG. 1 is configured to provide an interface between system 10 and a user (e.g., user 108, subject 106, a caregiver, a therapy decision-maker, etc.) through which the user can provide information to and receive information from system 10. This enables data, results, and/or instructions and any other communicable items, collectively referred to as "information," to be communicated between the user and system 10. An example of information that may be conveyed to user 108 is a report detailing quantitative information pertaining to individual inexsufflations throughout a period during which the subject is receiving treatment and/or therapy. Examples of interface devices suitable for inclusion in user interface 120 include a keypad, buttons, switches, a keyboard, knobs, levers, a display screen, an electronic display 150 configured to display information, a touch screen, speakers, a microphone, an indicator light, an audible alarm, and a printer. Information may be provided to user 108 or subject 106 by user interface 120 in the form of auditory signals, visual signals, tactile signals, and/or other sensory signals. Although electronic display 150 is depicted in FIG. 1 as a separate entity from user interface 120, this is for illustrative purposes only. In some embodiments, electronic display 150 may be integrated, embedded, and/or combined with user interface 120.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

One or more sensors 142 of system 10 in FIG. 1 are configured to generate output signals conveying measurements related to parameters of respiratory airflow and/or airway mechanics. These parameters may include one or more of flow, (airway) pressure, humidity, velocity, acceleration, and/or other gas or respiratory parameters. These parameters may pertain to one or more gas levels of the pressurized flow of breathable gas provided through pressure generator 140 and/or a flow of gas at or near the airway of subject 106, for example within subject interface appliance 184. As depicted in FIG. 1, one or more sensors 142 may be in fluid communication with conduit 182 and/or subject interface appliance 184. In some embodiments, one or more sensors 142 may generate output signals related to physiological parameters pertaining to subject 106.

The illustration of sensor 142 including two members in FIG. 1 is not intended to be limiting. The illustration of a sensor 142 at or near subject interface appliance 184 is not intended to be limiting. The illustration of a sensor 142 at or near pressure generator 140 is not intended to be limiting. In one embodiment sensor 142 includes a plurality of sensors operating as described above by generating output signals conveying information related to parameters associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or coupled with) such as valve drive current, rotor speed, motor speed, blower speed, fan speed, or a related measurement that may serve as a proxy for any of the previously listed parameters through a previously known and/or calibrated mathematical relationship. Resulting signals or information from one or more sensors 142 may be transmitted to processor 110, user interface 120, electronic storage 130, and/or other components of system 10. This transmission may be wired and/or wireless.

Processor 110 of system 10 in FIG. 1 is configured to provide information processing capabilities in system 10. As such, processor 110 includes one or more of a digital processor, an analog processor, a digital circuit designed to process information, an analog circuit designed to process information, a state machine, and/or other mechanisms for electronically processing information. Although processor 110 is depicted in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of control module 111, parameter determination module 112, interface module 113, metric storage module 114, and/or other modules. Processor 110 may be configured to execute modules 111-114 by software; hardware; firmware; some combination of software, hardware, and/or firmware; and/or other mechanisms for configuring processing capabilities on processor 110.

It should be appreciated that although modules 111-114 are illustrated in FIG. 1 as being co-located within a single processing unit, in embodiments in which processor 110 includes multiple processing units, one or more of modules 111-114 may be located remotely from the other modules. The description of the functionality provided by the different modules 111-114 described herein is for illustrative purposes, and is not intended to be limiting, as any of modules 111-114 may provide more or less functionality than is described. For example, one or more of modules 111-114 may be eliminated, and some or all of its functionality may be incorporated, shared, integrated into, and/or otherwise provided by other ones of modules 111-114. Note that processor 110 may be configured to execute one or more additional modules that may perform some or all of the functionality attributed below to one of modules 111-114.

Parameter determination module 112 of system 10 in FIG. 1 is configured to determine one or more gas parameters, respiratory parameters, and/or other parameters from output signals generated by sensor(s) 142. The one or more gas parameter may include and/or be related to one or more of (peak) flow, flow rate, (tidal) volume, pressure, temperature, humidity, velocity, acceleration, gas composition (e.g. concentration(s) of one or more constituents such as, e.g., $CO_2$), thermal energy dissipated, (intentional) gas leak, and/or other measurements related to the (pressurized) flow of breathable gas. One or more respiratory parameters may be derived from gas parameters and/or other output signals conveying measurements of the pressurized flow of breathable gas. The one or more respiratory parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), peak cough flow, average (or otherwise aggregated) cough flow, inspiratory tidal volume (for one or more respiratory cycles), expiratory tidal volume (for one or more respiratory cycles), and/or other respiratory parameters. Respiratory parameters may be determined on a breath-by-breath basis, on a cough-by-cough basis, and/or at other intervals.

For example, a peak cough flow parameter may be determined for individual respiratory cycles and/or individual inexsufflations. The peak cough flow parameter may be used as a basis for a determination how effectively subject 106 is able to clear secretions, how clear the airway of subject 106 is, and/or any other determination related to inexsufflation, respiratory therapy, and/or the condition of subject 106. For example, inspiratory tidal volume may be determined for individual respiratory cycles and/or individual inexsufflations. The inspiratory tidal volume may be used as a basis for a determination how effectively subject 106 is able to clear secretions, how clear the airway of subject 106 is, and/or any other determination related to inexsufflation, respiratory therapy, and/or the condition of subject 106. Using other parameters described herein in forming such a determination is contemplated within the scope of this disclosure. It is noted that by virtue of the systems and methods of inexsufflating subjects as described herein, such a determination may be formed by objective standards.

In some embodiments, determination of the peak cough flow parameter (and/or other parameters as described herein) by parameter determination module 112 may account and/or compensate for a length of conduit 182 (and/or volume of breathable gas within one or more components of delivery circuit 180) used between a particular sensor 142 and the airway of subject 106. For example, as depicted in FIG. 1, a sensor 142 used to generate output signals conveying information related to the peak cough flow parameter may be disposed at or near pressure generator 140, which may be separated from the airway of subject 106 by, at least, a predetermined length of conduit 182 (and thus a predetermined volume of breathable gas therewithin). The length of conduit 182 may be about 3 feet, about 4 feet, about 6 feet, about 9 feet, about 12 feet, and/or other length. Common pertinent lengths of conduit 182 in mechanical ventilation systems may be between about 6 feet and about 9 feet. Parameter determination module 112 may be calibrated accordingly as compensation for the part of delivery circuit 180 disposed between a particular sensor 142 and the airway of subject 106.

In some embodiments, parameter determination module 112 is configured to determine one or more of $SpO_2$ level, heart rate, respiratory rate, VC, EVC, IVC, FEV0.75, FEV1, FEV3, FEV6, FVC, FEV0.75/VC, FEV0.75/FVC, FEV1/VC, FEV1%, FEV3/VC, FEV0.75/FEV6, FEV1/FEV6, MEF75, MEF50, MEF25, MMEF, MEF50/VC, MEF50/FVC, MVV, FIV1, FIVC, PIF, FIV1%, MIF25, MIF50, MIF75, R50, MET, TV, ERV, IRV, IC, FRC, RV, TLC, FRC/TLC, RV/TLC, and/or other parameters, as well as any combinations/ratios thereof. One or more of these parameters may be displayed using user interface 120, electronic display 150, and/or interface module 113, and/or stored using electronic storage 130 and/or metric storage module 114, as described elsewhere herein.

Control module 111 of system 10 in FIG. 1 is configured to control operation of system 10 during inexsufflation of subject 106. Control module 111 may be configured to control pressure generator 140 to adjust one or more levels of one or more gas parameters of the pressurized flow of breathable gas in accordance with one or more of a (respiratory) therapy regimen, one or more algorithms that control adjustments and/or changes in the pressurized flow of breathable gas, and/or other factors. Control module 111 may be configured to control pressure generator 140 such that one or more gas parameters of the pressurized flow of breathable gas are varied over time in accordance with a respiratory therapy regimen and/or treatment. Control module 111 may be configured to control pressure generator 140 to provide the pressurized flow of breathable gas at inhalation pressure levels during inhalation phases, and/or at exhalation pressure levels during exhalation phases. For example, pressure of the pressurized flow of breathable gas may be elevated (e.g., about ambient atmosphere) during inhalation to insufflate subject 106. During this insufflation, one or more of a flow rate, an insufflation pressure, and/or an inhaled volume may be controlled by control module 111. Responsive to the insufflation being completed (e.g., as determined in accordance with the therapy regimen), control module 111 may be configured to cause pressure generator 140 to reduce pressure of the pressurized flow of breathable gas (e.g., to below ambient atmosphere and/or to a negative pressure, or some other pressure lower than the insufflation pressure) to cause the gas in the lungs and/or airway of subject 106 to be expelled and/or drawn out quickly, thereby exsufflating subject 106.

Parameters determined by parameter determination module 112 and/or received through one or more sensors 142 may be used by control module 111, e.g. in a feedback manner, to adjust therapy modes/settings/operations of system 10. Alternatively, and/or simultaneously, signals and/or information received through user interface 120 may be used by control module 111, e.g. in a feedback manner, to adjust one or more therapy modes/settings/operations of system 10. In some embodiments, user 108 may (e.g. manually) control one or more pressure levels used during operation of system 10 through user interface 120. Control module 111 may be configured to time its operations relative to the transitional moments in the breathing cycle of a subject, over multiple breath cycles, and/or in any other relation to any detected events and/or occurrences.

In some embodiments, operation of control module 111 may be governed through programmatic control, e.g. by an algorithm implemented through instructions that are executed by control module 111. Such an algorithm may be designed to titrate operating conditions of system 10 such that a target operating condition is reached and/or accomplished over time. For example, the algorithm may use a target peak cough flow for individual inexsufflations. The algorithm may adjust one or more gas parameters of the pressurized flow of breathable gas, such as for example the inspiratory pressure level, based on the determine peak cough flow parameter of one or more recent inexsufflations. In some embodiments, alternatively and/or simultaneously, the algorithm may be designed to reach a target inspiratory tidal volume for individual inexsufflations.

Interface module 113 of system 10 in FIG. 1 is configured to control user interface 120 and/or electronic display 150 to display information. The displayed information may pertain to (or be based on) one or more of the generated output signals, one or more parameters as determined by parameter determination module 112, including but not limited to the peak cough flow parameter and the inspiratory tidal volume, and/or other information. In some embodiments, the displayed information may be an aggregation of one or more determined parameters. In some embodiments, the displayed information may be displayed in real-time, thus providing immediate feedback on the operation of system 10 and/or the efficacy of the treatment while the treatment is being administered to subject 106.

Metric storage module 114 of system 10 in FIG. 1 is configured to derive, determine, and/or store information on electronic storage 130. The derived, determined, and/or stored information may be based on one or more generated output signals from one or more sensors 142, one or more determined parameters from parameter determination module 112, one or more operating conditions of system 10 as controlled through control module 111, and/or other information related to the operation of system 10. For example, metric storage module 114 may be configured to derive and/or determine metrics based on individual inexsufflations, sets of such inexsufflations, individual treatments including one or more of such inexsufflations, sets of such treatments, days including one or more such treatments, and/or other periods of treatment time including one or more such individual inexsufflations. Metric storage module 114 may be configured to subsequently store such metrics and/or other information as described herein on electronic storage.

In some embodiments, the derived and/or stored metrics include one or more of number of coughs per treatment, number of treatments per day, number of days or treatment, average (or otherwise aggregated) peak cough flow per treatment, average (or otherwise aggregated) peak cough flow per day that includes one or more treatments, average (or otherwise aggregated) inspiratory tidal volume, average (or otherwise aggregated) delivered pressure level for insufflation and/or exsufflation per individual inexsufflation, treatment, and/or day that includes one or more treatments, and/or other information pertaining to the treatment described herein.

In some embodiments, the information stored by metric storage module 114 may be an aggregation of one or more determined parameters. In some embodiments, the stored information is stored on removable electronic storage such that review and/or analysis may be performed after one or more treatments. For example, the stored information may be reviewed at a doctor's office, by virtue of using a software application, and/or remotely through a network-connected computing platform. Such review and/or analysis may reveal trends in one or more parameters over time. Such review and/or analysis may be used to adjust a therapy regimen for subject 106. Such review and/or analysis may be used to verify and/or quantify a level of compliance with a prescribed therapy regimen.

In some embodiments, system 10 may transfer the stored information, e.g. through removable electronic storage and/or a network connection, to a client computing platform configured to perform the review and/or analysis described herein. Such a client computing platform may be further configured to present the stored information, and/or any results from the described review and/or analysis, to a user of the client computing platform, e.g. user 108. By way of non-limiting example, a client computing platform may include one or more of a desktop computer, a laptop computer, a tablet computing device, a handheld computer, a NetBook, a smartphone, a gaming console, an interactive television, and/or other computing platform or computing device.

It will be appreciated that the description of the operation of pressure generator 140 by the electronic processor 110 and/or its modules is not intended to be limiting. Other controllers for opening pressure generator 140 responsive to pressurization along delivery circuit 180 fall within the scope of this disclosure. Other mechanical controllers are also contemplated.

Figure 2:
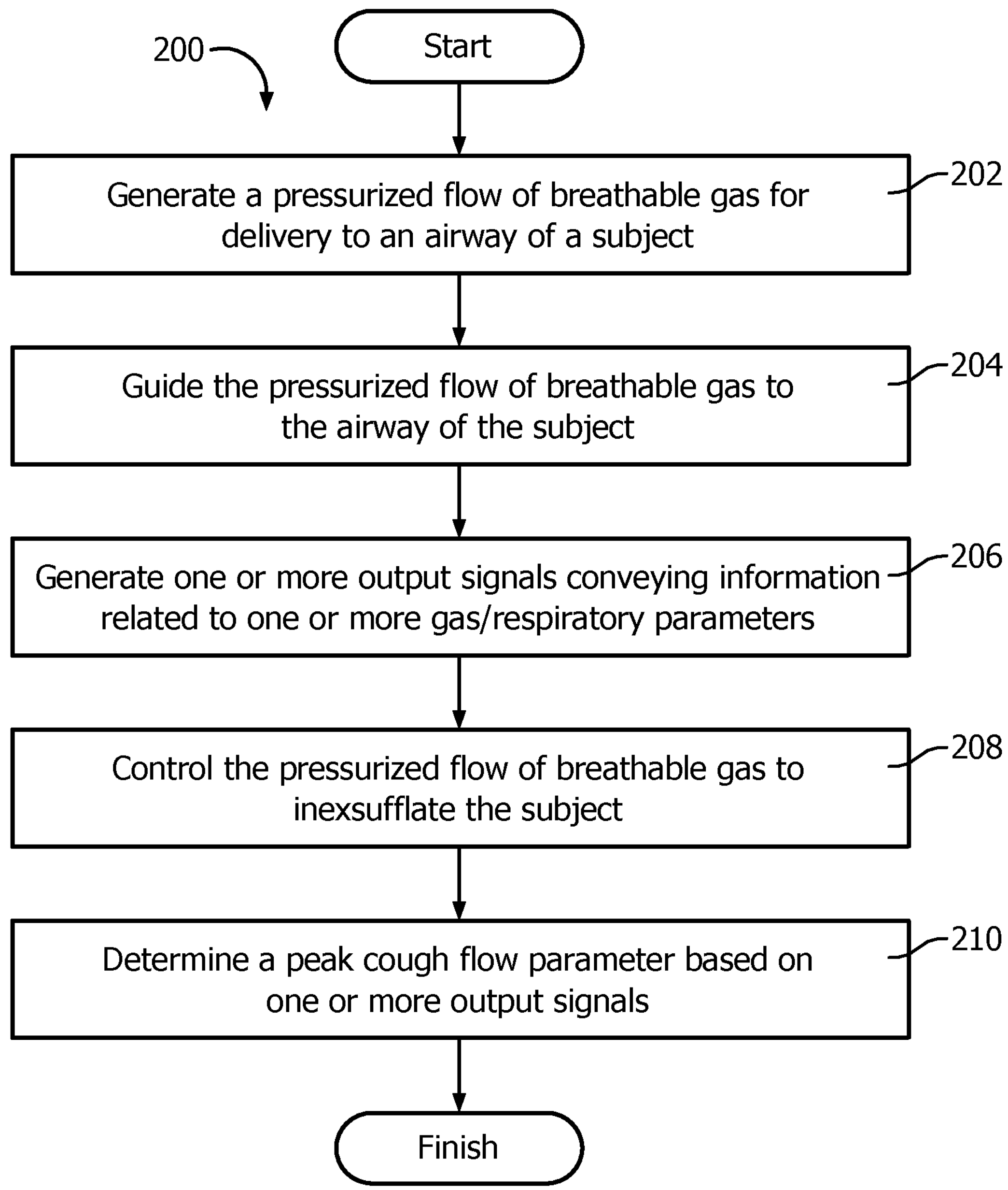
FIG. 2 illustrates a method of inexsufflating a subject according to one or more embodiments.

FIG. 2 illustrates a method 200 of inexsufflating a subject. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 2 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, a pressurized flow of breathable gas is generated for delivery to the airway of a subject. In some embodiments, operation 202 is performed by a pressure generator the same as or similar to pressure generator 140 (shown in FIG. 1 and described herein).

At an operation 204, the pressurized flow of breathable gas is guided to the airway of the subject. In some embodiments, operation 204 is performed by a delivery circuit the same as or similar to delivery circuit 180 (shown in FIG. 1 and described herein).

At an operation 206, one or more output signals are generated that convey information related to one or more parameters, wherein the one or more parameters include one or both of a gas parameter and/or a respiratory parameter. In some embodiments, operation 206 is performed by a sensor the same as or similar to sensor 142 (shown in FIG. 1 and described herein).

At an operation 208, the pressurized flow of breathable gas is controlled to inexsufflate the subject. In some embodiments, operation 208 is performed by a control module the same as or similar to control module 111 (shown in FIG. 1 and described herein).

At an operation 210, a peak cough flow parameter is determined based on the one or more generated output signals. In some embodiments, operation 210 is performed by a parameter determination module the same as or similar to parameter determination module 112 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to in-exsufflate a subject, the system comprising:

a pressure generator configured to generate a pressurized flow of breathable gas for delivery to an airway of the subject;

a subject interface configured to guide the pressurized flow of breathable gas to the airway of the subject;

one or more sensors configured to generate one or more output signals conveying information related to one or more parameters, wherein the one or more parameters include one or both of a gas parameter and/or a respiratory parameter;

an electronic display configured to display information; and one or more processors configured to execute computer program modules, the computer program modules comprising:

a control module configured to control the pressure generator to provide an inexsufflation to the subject;

a parameter determination module configured to determine a peak cough flow parameter during the inexsufflation, wherein the determination is based on the one or more output signals; and an interface module configured to control the electronic display to display the peak cough flow parameter for individual inexsufflations while the subject is receiving therapy, the peak cough flow parameter displayed for individual inexsufflations comprising an indication of an effectiveness of an individual inexsufflation at clearing secretions from the airway of the subject, the indication of the effectiveness quantifying a change in the peak cough flow parameter from one insufflation to a next insufflation;

wherein the control module is configured to cause the pressure generator to adjust one or more parameters of the pressurized flow of breathable gas based on two or more of the determined peak cough flow parameters from two or more inexsufflations, wherein the parameter determination module is further configured to determine one or more aggregated parameters based on the one or more output signals, the one or more aggregated parameters comprising a number of coughs per treatment, average peak cough flow per treatment, and/or average peak cough flow per day that includes one or more treatments, and wherein said adjusting one or more parameters of the pressurized flow of breathable gas is further based on the determined aggregated parameters; wherein a treatment comprises one or more inexsufflations.

2. The system of claim 1, wherein the determination of the peak cough flow parameter is based on a length of a conduit of the subject interface disposed between the one or more sensors and the airway of the subject.

3. The system of claim 1, wherein the parameter determination module is configured such that the peak cough flow parameter is inspiratory tidal volume, and wherein the display comprises changes in the inspiratory tidal volume for the individual inexsufflations.

4. The system of claim 1, further comprising:

electronic storage comprising electronic storage media configured to electronically store information; and a metric storage module configured to determine and store the information based on the one or more generated output signals, wherein the information based on the one or more generated output signals is stored on the electronic storage; wherein the determined and stored information comprises one or more metrics including one or more of a number of treatments per day; a number of days of treatment; or average delivered pressure level for insufflation and/or exsufflation per individual treatment, and/or day that includes one or more treatments.

5. The system of claim 1, wherein the control module is configured to cause the pressure generator to adjust one or more parameters of the pressurized flow of breathable gas based on comparisons of the determined peak cough flow parameters from the plurality of inexsufflations to a target peak cough flow parameter, wherein the control module is configured to cause the pressure generator to adjust the one or more parameters after the plurality of inexsufflations without an intervening adjustment during or between individual inexsufflations in the plurality of inexsufflations.

6. A method of determining a peak cough flow parameter during an inexsufflation of a subject, the method comprising;

generating a pressurized flow of breathable gas for delivery to an airway of the subject;

guiding the pressurized flow of breathable gas to the airway of the subject;

generating one or more output signals by one or more sensors conveying information related to one or more parameters, wherein the one or more parameters include one or both of a gas parameter and/or a respiratory parameter;

controlling the pressurized flow of breathable gas to provide an inexsufflation to the subject;

determining a peak cough flow parameter during the inexsufflation, wherein the step of determining is based on the one or more output signals;

displaying the peak cough flow parameter for individual inexsufflations while the subject is receiving therapy, the peak cough flow parameter displayed for individual inexsufflations comprising an indication of an effectiveness of an individual inexsufflation at clearing secretions from the airway of the subject, the indication of the effectiveness quantifying a change in the peak cough flow parameter from one insufflation to a next insufflation;

adjusting one or more parameters of the pressurized flow of breathable gas based on two or more of the determined peak cough flow parameters from two or more inexsufflations; and determining one or more aggregated parameters based on the one or more output signals, the one or more aggregated parameters comprising a number of coughs per treatment, average peak cough flow per treatment, and/or average peak cough flow per day that includes one or more treatments, and wherein said adjusting the one or more parameters of the pressurized flow of breathable gas is further based on the determined aggregated parameters; wherein a treatment comprises one or more inexsufflations.

7. The method of claim 6, wherein the peak cough flow parameter is determined based on a length of a conduit disposed between the one or more sensors and the airway of the subject.

8. The method of claim 6, wherein the peak cough flow parameter is inspiratory tidal volume, and wherein the displaying comprises displaying changes in the inspiratory tidal volume for the individual inexsufflations.

9. The method of claim 6, further comprising determining and storing the information based on the one or more generated output signals, wherein the determined and stored information comprises one or more metrics including one or more of a number of treatments per day; a number of days of treatment; or average delivered pressure level for insufflation and/or exsufflation per individual treatment, and/or day that includes one or more treatments.

10. The method of claim 6, wherein the adjusting comprises adjusting the one or more parameters of the pressurized flow of breathable gas based on comparisons of the determined peak cough flow parameters from the plurality of inexsufflations to a target peak cough flow parameter, wherein the adjusting is after the plurality of inexsufflations without an intervening adjustment during or between individual inexsufflations in the plurality of inexsufflations.

11. A system configured for inexsufflating a subject, the system comprising:

pressure means for generating a pressurized flow of breathable gas for delivery to an airway of the subject;

means for guiding the pressurized flow of breathable gas to the airway of the subject;

sensor means for generating one or more output signals conveying information related to one or more parameters, wherein the one or more parameters include one or both of a gas parameter and/or a respiratory parameter;

means for presenting information for display;

means for controlling the pressure means to provide an inexsufflation to the subject;

means for determining configured to determine a peak cough flow parameter during inexsufflation, wherein the determination is based on the one or more output signals;

means for controlling the means for presenting information to display the peak cough flow parameter for individual inexsufflations while the subject is receiving therapy, the peak cough flow parameter displayed for individual inexsufflations comprising an indication of an effectiveness of an individual inexsufflation at clearing secretions from the airway of the subject, the indication of the effectiveness quantifying a change in the peak cough flow parameter from one insufflation to a next insufflation; and means for causing the pressure means to adjust one or more parameters of the pressurized flow of breathable gas based on two or more of the determined peak cough flow parameters from two or more inexsufflations, means for determining further configured to determine one or more aggregated parameters based on the one or more output signals, the one or more aggregated parameters comprising a number of coughs per treatment, average peak cough flow per treatment, and/or average peak cough flow per day that includes one or more treatments, and wherein said adjusting the one or more parameters of the pressurized flow of breathable gas is further based on the determined aggregated parameters; wherein a treatment comprises one or more inexsufflations.

12. The system of claim 11, wherein the peak cough flow parameter is determined based on a length of conduit used between the sensor means and the airway of the subject.

13. The system of claim 11, wherein the peak cough flow parameter is inspiratory tidal volume, and wherein the presented information comprises changes in the inspiratory tidal volume for the individual inexsufflations.

14. The system of claim 11, further comprising means for determining and storing the information based on the one or more generated output signals, wherein the determined and stored information comprises one or more metrics including one or more of a number of treatments per day; a number of days of treatment; or average delivered pressure level for insufflation and/or exsufflation per individual treatment, and/or day that includes one or more treatments.

15. The system of claim 11, wherein adjusting the one or more parameters of the pressurized flow of breathable gas is based on comparisons of the determined peak cough flow parameters from the plurality of inexsufflations to a target peak cough flow parameter, wherein the adjusting is after the plurality of inexsufflations without an intervening adjustment during or between individual inexsufflations in the plurality of inexsufflations.

* * * * *